United States Patent
Wheeler (10) Patent No.: US 10,215,677 B2
(45) Date of Patent: Feb. 26, 2019

(54) VERIFICATION OF A METER SENSOR FOR A VIBRATORY METER

(71) Applicant: Micro Motion, Inc., Boulder, CO (US)

(72) Inventor: Simon P. H. Wheeler, Erie, CO (US)

(73) Assignee: Micro Motion, Inc., Boulder, CO (US)

( * ) Notice: Subject to any disclaimer, the term of this patent is extended or adjusted under 35 U.S.C. 154(b) by 78 days.

(21) Appl. No.: 14/778,958

(22) PCT Filed: Apr. 3, 2014

(86) PCT No.: PCT/US2014/032806
§ 371 (c)(1),
(2) Date: Sep. 21, 2015

(87) PCT Pub. No.: WO2014/172111
PCT Pub. Date: Oct. 23, 2014

(65) Prior Publication Data
US 2016/0061707 A1 Mar. 3, 2016

Related U.S. Application Data (60) Provisional application No. 61/813,495, filed on Apr. 18, 2013.

(51) Int. Cl.
*G01N 9/00* (2006.01)
*G01N 9/36* (2006.01)
(Continued)

(52) U.S. Cl.
CPC ............... *G01N 9/36* (2013.01); *G01H 17/00* (2013.01); *G01N 9/002* (2013.01); *G01N 11/16* (2013.01);
(Continued)

(58) Field of Classification Search
CPC . G01N 9/36; G01N 9/10; G01N 11/16; G01N 29/036; G01N 29/326;
(Continued)

(56) References Cited

U.S. PATENT DOCUMENTS

| 3,902,355 A | 9/1975 | Weisser |
| 4,734,609 A | 3/1988 | Jasmine |

(Continued)

FOREIGN PATENT DOCUMENTS

| EP | 0222503 A1 | 5/1987 |
| EP | 1925916 A2 | 5/2008 |

(Continued)

OTHER PUBLICATIONS

Recommended Practice for Maintenance, Testing, and Replacement of Vented Lead-Acid Batteries for Stationary Applications, in IEEE Std 450-2010 (Revision of IEEE Std 450-2002), vol., No., pp. 1-71, Feb. 25, 2011 doi: 10.1109/IEEESTD.2011.5724325.*

*Primary Examiner* — Natalie Huls
*Assistant Examiner* — Monica S Young
(74) *Attorney, Agent, or Firm* — The Ollila Law Group LLC (57) ABSTRACT

A vibratory meter and method for verification of a vibratory sensor is provided. The method includes measuring a plurality of temperatures using a temperature sensor and measuring a plurality of sensor time periods using the sensor assembly. An average temperature and an average sensor time period are determined. The average sensor time period is compensated using the average temperature, generating a compensated sensor time period. The compensated sensor time period is compared to a reference sensor time period. The results are indicated. In further embodiments, a standard deviation of the plurality of temperatures or the plurality of sensor time periods are compared to a limit and sensor stability is indicated. In further embodiments, a difference between measured density and a reference density of a fluid is compensated using the altitude and the average temperature.

17 Claims, 5 Drawing Sheets

(51) Int. Cl.
- *G01N 11/16* (2006.01)
- *G01N 29/036* (2006.01)
- *G01N 29/32* (2006.01)
- *G01N 29/44* (2006.01)
- *G01H 17/00* (2006.01)
- *G01N 9/10* (2006.01)
- *G01N 11/00* (2006.01)

(52) U.S. Cl.
CPC ......... *G01N 29/036* (2013.01); *G01N 29/326* (2013.01); *G01N 29/4436* (2013.01); *G01N 9/10* (2013.01); *G01N 2009/006* (2013.01); *G01N 2011/002* (2013.01); *G01N 2011/0006* (2013.01); *G01N 2011/0013* (2013.01); *G01N 2291/02818* (2013.01)

(58) Field of Classification Search
CPC ......... G01N 29/4436; G01N 2009/006; G01N 2011/0006; G01N 2016/0013; G01N 2011/002; G01N 2291/02818; G01H 17/00
USPC .......................................................... 73/1.02
See application file for complete search history.

(56) References Cited

U.S. PATENT DOCUMENTS

| | | | |
|---|---|---|---|
| 5,570,300 A | 10/1996 | Henry et al. | |
| 5,687,100 A * | 11/1997 | Buttler | G01F 1/8413 702/100 |
| 2001/0045134 A1 * | 11/2001 | Henry | G01F 1/74 73/861.356 |
| 2003/0140712 A1 * | 7/2003 | Barger | G01F 1/8404 73/861.354 |
| 2006/0287839 A1 | 12/2006 | Dutton | |
| 2008/0281535 A1 * | 11/2008 | Rensing | G01F 1/8413 702/56 |
| 2010/0268469 A1 | 10/2010 | Harrison et al. | |
| 2012/0096923 A1 * | 4/2012 | Weinstein | G01F 1/74 73/19.03 |
| 2013/0081702 A1 * | 4/2013 | Mohammed | F17D 3/00 137/2 |
| 2013/0305837 A1 * | 11/2013 | Van Cleve | G01F 1/84 73/861.02 |
| 2016/0123792 A1 * | 5/2016 | Plaziak | G01F 25/0007 73/1.16 |
| 2017/0248094 A1 * | 8/2017 | Zimmer | F02D 41/22 |

FOREIGN PATENT DOCUMENTS

| | | | |
|---|---|---|---|
| EP | 2565594 A1 | 3/2013 | |
| JP | 2002-062175 | 2/2002 | |
| JP | 2008-102155 | 5/2008 | |
| WO | 2005040733 A1 | 5/2005 | |
| WO | WO 2012115639 A1 * | 8/2012 | G01F 1/84 |
| WO | 2013006171 A1 | 1/2013 | |
| WO | 2013009307 A1 | 1/2013 | |

* cited by examiner

VERIFICATION OF A METER SENSOR FOR A VIBRATORY METER

TECHNICAL FIELD

The present invention relates to vibrating element meters, and more particularly, to a method and apparatus for validating a sensor assembly of a vibrating element meter.

BACKGROUND OF THE INVENTION

Vibrating meters, such as for example, liquid density meters, gas density meters, liquid viscosity meters, gas/liquid specific gravity meters, gas/liquid relative density meters, and gas molecular weight meters, are generally known and are used for measuring characteristics of fluids. Generally, meters comprise a sensor assembly and an electronics portion. The material within the sensor assembly may be flowing or stationary. Each type of sensor may have unique characteristics, which a meter must account for in order to achieve optimum performance. For example, some sensors may require a tube apparatus to vibrate at particular displacement levels. Other sensor assembly types may require special compensation algorithms.

The meter electronics, among performing other functions, typically include stored sensor calibration values for the particular sensor being used. For example the meter electronics may include a reference sensor time period (i.e. the inverse of the reference resonant frequency). The reference sensor time period represents a fundamental measurement performance of the sensor geometry for a specific sensor assembly, as measured in the factory under reference conditions. A change between a sensor time period measured after a vibrating element meter is installed at a customer site and a reference sensor time period may represent physical change in the sensor assembly due to coating, erosion, corrosion, or damage to the vibrating element sensor, in addition to other causes.

A commonly used technique to monitor a change of sensor time period in vibratory meters is to perform an air-point health check, a vacuum-point health check, or a health check using any fluid having an accurately known density. In any of the three health check methodologies, a meter is taken off-line and placed under test conditions. The meter is sometimes cleaned before being placed under test conditions, either through mechanical or solvent-based techniques. Either a liquid or gas meter may next be placed under a vacuum or filled with a fluid having an accurately known density, such as air or water. For a liquid meter, the test conditions commonly include placing the meter under ambient air conditions. For a gas meter, the test conditions commonly include placing the meter under vacuum conditions. The sensor time period is then determined and compared to the reference sensor time period measurement.

Typically, test measurements are taken under conditions that may be different from the reference conditions of a health check test. The sensor time period measured during a health check may therefore reflect variations in vibrational response due not only to changes in a sensor assembly, but also due to differences between reference and test conditions. Current health check methodologies fail to isolate changes in vibrational response due to changes in the physical sensor assembly and changes in test conditions.

For example, the sensor time period measurement may be affected by temperature. The first reason that temperature may affect a sensor time period is because temperature may affect the stiffness of the sensor assembly itself. The second reason is because the density of fluid moving in a sensor assembly may be dependent on temperature. A third mechanism that temperature may affect the robustness of a health check is if the sensor assembly is not at a stable temperature or if there is a temperature drift. None of these temperature effects are accounted for under the conventional vibratory sensor health check techniques, which may lead to false indications that a sensor assembly is either faulty or healthy. Errors may lead to incorrect customer decisions and unnecessary service calls.

What is needed is a sensor health assessment that corrects for variations in measured sensor time period due to temperature, pressure, and density. What is also needed is a method to determine whether a sensor assembly is stable enough to provide an accurate result from an air-point health check, a vacuum-point health check, or a health check using another fluid.

SUMMARY OF THE APPLICATION

A vibrating element meter for meter health verification is provided. The vibrating element meter includes a sensor assembly, at least one temperature sensor, and meter electronics. The sensor assembly includes a vibrating member, a pickoff/detection sensor, and a driver configured to vibrate the vibrating member. The meter electronics is coupled to the pickoff/detection sensor, the driver, and the at least one temperature sensor. The meter electronics is configured to measure a plurality of temperatures using the at least one temperature sensor. The meter electronics is further configured to measure a plurality of sensor time periods using the sensor assembly. The meter electronics is further configured to determine an average temperature from the plurality of temperatures. The meter electronics is further configured to determine an average sensor time period from the plurality of sensor time periods. The meter electronics is further configured to compensate the average sensor time period using the average temperature to generate a compensated sensor time period. The meter electronics is further configured to compare the compensated sensor time period to a reference sensor time period. The meter electronics is further configured to indicate whether the compensated sensor time period is within a sensor time period error limit of the reference sensor time period.

A method for verification of a sensor is provided. The method includes the step of measuring a plurality of temperatures using at least one temperature sensor and a plurality of sensor time periods using a sensor assembly. The sensor assembly includes a vibrating member, a pickoff/detection sensor, and a driver configured to vibrate the vibrating member. The method further comprises the step of determining an average temperature from the plurality of temperatures. The method further comprises the step of determining an average sensor time period from the plurality of sensor time periods. The method further comprises the step of compensating the average sensor time period using the average temperature to generate a compensated sensor time period. The method further comprises the step of comparing the compensated sensor time period to a reference sensor time period. The method further comprises the step of indicating whether the compensated sensor time period is within a sensor time period error limit of the reference sensor time period.

A method for health verification of a sensor is provided. The method includes the step of measuring a plurality of temperatures using at least one temperature sensor and a plurality of sensor time periods using a sensor assembly. The sensor assembly includes a vibrating member, a pickoff/detection sensor, and a driver configured to vibrate the vibrating member. The method further comprises the step of calculating a first standard deviation using a first data set comprising one of the plurality of temperatures or the plurality of sensor time periods. The method further comprises the step of comparing the first standard deviation to a first limit. The method further comprises the step of indicating whether the first standard deviation is greater than the first limit.

A method for health verification of a sensor is provided. The method includes the step of measuring a plurality of temperatures using at least one temperature sensor and a plurality of sensor time periods using a sensor assembly. The sensor assembly includes one or more vibrating elements, one or more pickoff/detection sensors, and a driver configured to vibrate the one or more vibrating elements. The method further includes the step of determining an average temperature from the plurality of temperatures. The method further includes the step of determining an average sensor time period from the plurality of sensor time periods. The method further includes the step of receiving an altitude. The method further includes the step of measuring a density of a fluid using the sensor assembly. The method further includes the step of compensating the sensor time period for a difference in density between the reference density and the measured density using the altitude and the average temperature.

ASPECTS OF THE APPLICATION

Preferably, measuring the plurality of temperatures using the temperature sensor and the plurality of sensor time periods using the sensor assembly further includes cleaning the sensor assembly.

Preferably, measuring the plurality of temperatures using the temperature sensor and the plurality of sensor time periods using the sensor assembly further includes filling the sensor assembly with ambient air.

Preferably, measuring the plurality of temperatures using the temperature sensor and the plurality of sensor time periods using the sensor assembly further includes placing the sensor assembly under a vacuum.

Preferably, measuring the plurality of temperatures using the temperature sensor and the plurality of sensor time periods using the sensor further includes filling the sensor assembly with or inserting the sensor assembly into a fluid having an accurately known density.

Preferably, the meter electronics is further configured to calculate a standard deviation using one of the plurality of temperatures and the plurality of sensor time periods, compare the standard deviation to a limit, and indicate whether the standard deviation is greater than the limit.

Preferably, the meter electronics is further configured to receive an altitude, and compensate the compensated sensor time period using the altitude.

Preferably, the meter electronics is further configured to measure a density of a fluid using the sensor assembly, and compensate the compensated sensor time period for a difference in density between the reference density and the measured density using the altitude and the average temperature.

Preferably, the method further includes the steps of calculating a second standard deviation using a second data set comprising one of the plurality of temperatures or the plurality of sensor time periods, wherein the first data set is different from the second data set, comparing the second standard deviation to a second limit, and indicating whether the second standard deviation is greater than the second limit.

BRIEF DESCRIPTION OF THE DRAWINGS

The same reference number represents the same element on all drawings. The drawings are not necessarily to scale.

DETAILED DESCRIPTION

FIGS. 1-5 and the following description depict specific examples to teach those skilled in the art how to make and use the best mode of the Application. For the purpose of teaching inventive principles, some conventional aspects have been simplified or omitted. Those skilled in the art will appreciate variations from these examples that fall within the scope of the Application. Those skilled in the art will appreciate that the features described below may be combined in various ways to form multiple variations of the Application. As a result, the Application is not limited to the specific examples described below, but only by the claims and their equivalents.

Figure 1:
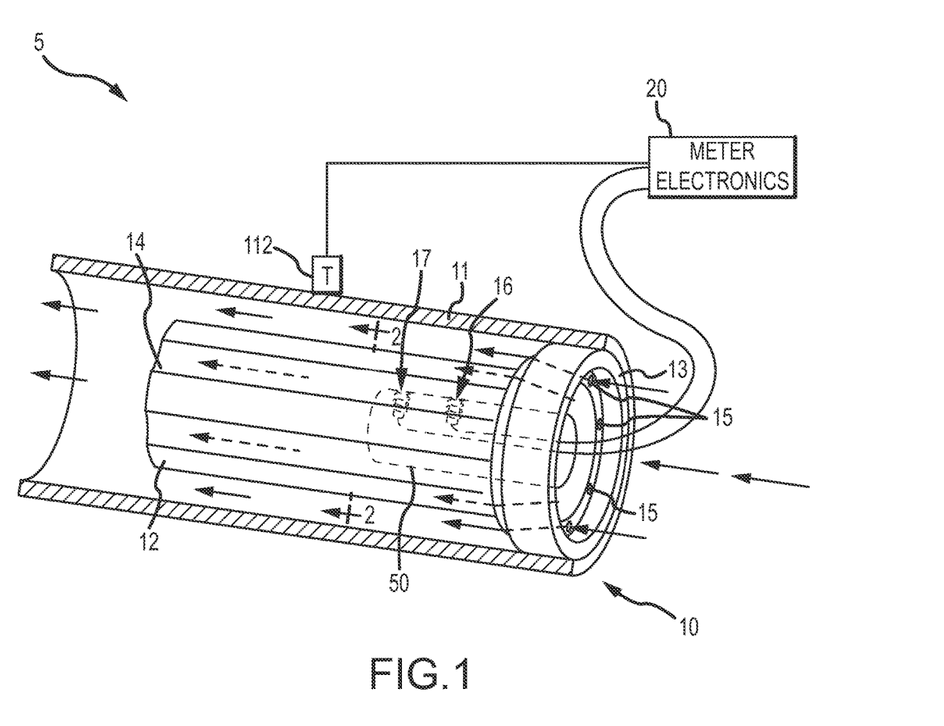
FIG. 1 depicts vibrating element meter 5 according to an embodiment of the Application.

FIG. 1 shows a vibrating element meter 5, a density meter. The vibrating element meter 5 comprises a sensor assembly 10 and meter electronics 20. The embodiment of a density meter is not intended to be limiting, however. Those skilled in the art will readily recognize that embodiments of the Application described herein may be applied to the verification of liquid density meters, gas density meters, liquid viscosity meters, gas/liquid specific gravity meters, gas/liquid relative density meters, gas molecular weight meters, and/or any type of vibrating meter.

The vibrating element meter 5 may be configured to measure a density of a fluid, such as a liquid or a gas, for example. The vibrating element meter 5 includes a housing 11 with a vibrating member 12 located at least partially within the housing 11. A portion of the housing 11 is cut away to show the vibrating member 12. The vibrating element meter 5 may be placed in-line in an existing pipeline, for example. Alternatively, the housing 11 may comprise closed ends with apertures to receive a fluid sample, for example. Therefore, while flanges are not shown, in many instances, the housing 11 or the vibrating member 12 may include flanges or other members for operatively coupling the vibrating element meter 5 to a pipeline or similar fluid delivering device in a fluid-tight manner. According to the example shown, the vibrating member 12 is cantilever mounted to the housing 11. The vibrating member 12 is shown coupled to the housing 11 at an inlet end 13 with the outlet end 14 free to vibrate.

According to the example shown, the vibrating member 12 also includes a plurality of fluid apertures 15 near the inlet end 13. The fluid apertures 15 can be provided to allow some of the fluid entering the vibrating element meter 5 to flow between the housing 11 and the vibrating member 12. Therefore, the fluid contacts the inside as well as the outside surfaces of the vibrating member 12. This is particularly helpful when the fluid under test comprises a gas because a greater surface area is exposed to the gas. In other examples, apertures may be provided in the housing 11 to expose the fluid under test to the outer surface of the vibrating member 12 and therefore, the apertures 15 are not required in the vibrating member 12.

Further shown in FIG. 1 is a driver 16 and a pickoff/detection sensor 17 positioned within a cylinder 50. The driver 16 and pickoff/detection sensor 17 are shown as comprising coils, which are well known in the art. If an electric current is provided to the coil, a magnetic field is induced in the vibrating member 12 causing the vibrating member 12 to vibrate. Conversely, the vibration of the vibrating member 12 induces a voltage in the pickoff/detection sensor 17. The driver 16 receives a drive signal from the meter electronics 20 in order to vibrate the vibrating member 12 at one of its resonant frequencies in one of a plurality of vibration modes, including for example simple bending, torsional, radial, or coupled type. The pickoff/detection sensor 17 detects the vibration of the vibrating member 12, including the frequency at which the vibrating member 12 is vibrating and sends the vibration information to the meter electronics 20 for processing. As the vibrating member 12 vibrates, the fluid contacting the vibrating member's wall vibrates along with the vibrating member 12. The added mass of the fluid contacting the vibrating member 12 lowers the resonant frequency. The new, lower, resonant frequency of the vibrating member 12 is used to determine the density of the fluid as is generally known in the art according to a previously determined correlation, for example.

Vibrating element meter 5 further includes temperature sensor 112. In embodiments, temperature sensor 112 is coupled to housing 11. In other embodiments, temperature sensor 112 may be coupled to driver 16, pickoff/detection sensor 17, inlet 13, or any other part of sensor assembly 10, however. In embodiments, vibrating element meter 5 may include more than one temperature sensor, and each respective temperature sensor may be coupled to the same or different components of the sensor assembly 10. The one or more signals provided by temperature sensors 112 may be combined in any manner commonly known to those skilled in the art to generate a one or more temperature measurement values.

Figure 2:
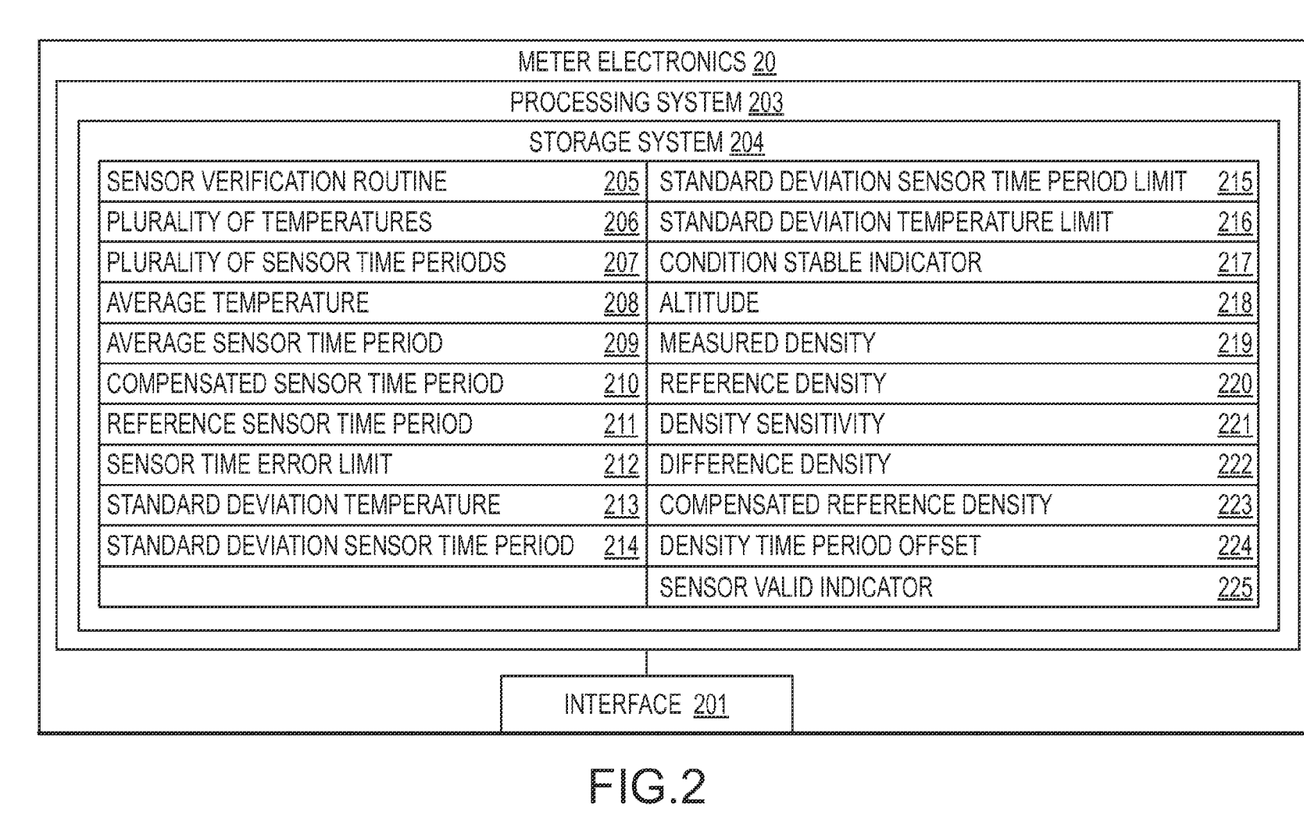
FIG. 2 depicts meter electronics 20 according to an embodiment of the Application.

FIG. 2 depicts meter electronics 20 of the vibrating element meter 5 according to an embodiment of the Application. Meter electronics 20 may include an interface 201 and a processing system 203. The processing system 203 may include a storage system 204. As previously discussed, meter electronics 20 may generate a drive signal to supply to driver 16 and receive signals from pickoff/detection sensor 17 and temperature sensor 112. In some embodiments, meter electronics 20 may receive signals from the driver 16. Meter electronics 20 may operate sensor assembly 10 as a density meter, a viscosity meter, or a flow meter such as a Coriolis mass flow meter. It should be appreciated that meter electronics 20 may also operate other types of vibrating meters, and the particular examples provided should not limit the scope of the present invention. Meter electronics 20 may process vibratory sensor signals in order to obtain one or more characteristics of the material in housing 11.

Interface 201 may receive sensor signals from the driver 16, pickoff/detection sensor 17, or temperature sensor 112, via leads. Interface 201 may perform any necessary or desired signal conditioning, such as any manner of formatting, amplification, buffering, etc. Alternatively, some or all of the signal conditioning may be performed in processing system 203. In addition, interface 201 may enable communications between meter electronics 20 and external devices. Interface 201 may be capable of any manner of electronic, optical, or wireless communication. In addition, interface 201 may enable communications between meter electronics 20 and external devices, for example. Interface 201 may be capable of any manner of electronic, optical, or wireless communication.

Interface 201 in one embodiment may include a digitizer (not shown), wherein sensor assembly 10 signals comprise analog sensor signals. The digitizer may sample and digitize the analog sensor signals and produce digital sensor signals. The digitizer may also perform any needed decimation, wherein the digital sensor signal is decimated in order to reduce the amount of signal processing needed and to reduce the processing time.

Processing system 203 conducts operations of meter electronics 20 and processes density/viscosity/flow measurements from sensor assembly 10. Processing system 203 may also execute one or more processing routines such as sensor verification routine 205.

Processing system 203 may comprise a general purpose computer, a micro-processing system, a logic circuit, or any other general purpose or customized processing device capable of performing the functions described herein. Processing system 203 may be distributed among multiple processing devices. Processing system 203 may include any manner of integral or independent electronic storage medium, such as storage system 204.

Storage system 204 may store meter parameters and data, software routines, constant values, and variable values. Storage system 204 may comprise a primary or main memory, such as a random access memory (RAM). In embodiments, storage system 204 may include a hard disk drive, a removable storage device, a memory card, a floppy disk drive, a magnetic tape drive, a compact disk drive, a digital versatile disc, a Blue-ray disc, an optical storage device, tape backup, or any other computer useable or readable storage medium.

It should be understood that meter electronics 20 may include various other components and functions that are generally known in the art. These additional features are omitted from the description and the figures for the purpose of brevity. Therefore, the present invention should not be limited to the specific embodiments shown and discussed.

While FIG. 1 depicts only a single sensor assembly 10 in communication with meter electronics 20, those skilled in the art will readily appreciate that multiple sensor assemblies may be in communication with meter electronics 20. Further, meter electronics 20 may be capable of operating a variety of different sensor types. Therefore, it is important to confirm that the particular sensor assemblies in communication with meter electronics 20 comprise valid sensors. Each sensor assembly, such as the sensor assembly 10 in communication with meter electronics 20, may have a respective section of storage system 204 dedicated to an air-point, a vacuum-point, or a fluid health check. For example, if a sensor assembly comprises a density meter, as in the example of sensor assembly 10, the calibration values may include a sensor time period value at reference conditions. Other sensor calibration values are contemplated and are included within the scope of the present invention.

Storage system 204 stores variables that may be used by sensor verification routine 205 to verify the health of sensor assembly 10. For example, storage system 204 stores a plurality of temperatures 206 and a plurality of sensor time periods 207. Plurality of temperatures 206 may be determined by obtaining a time series of measurements from the at least one temperature sensor 112. The plurality of sensor time periods 207 may be determined by driving a sensor assembly at its natural frequency and determining the inverse of the frequency of the greatest response. In the example of sensor assembly 10, driver 16 may oscillate vibrating member 12, generating signals at the pickoff/detection sensor 17 that may be used to determine a series of sensor time periods of sensor assembly 10. In embodiments, each temperature of the plurality of temperatures 206 may correspond to a respective sensor time period of the plurality of sensor time periods 207. For example, each respective temperature of the plurality of temperatures 206 and each respective sensor time period of the plurality of sensor time periods 207 may be measured at one second intervals for a period of 20 seconds.

Storage system 204 also stores an average temperature 208 and an average sensor time period 209. Average temperature 208 may be determined by averaging the plurality of temperatures 206. Average sensor time period 209 may be determined by averaging plurality of sensor time periods 207.

Storage system 204 also stores a compensated sensor time period 210. Compensated sensor time period 210 is a value that has been corrected for one or more physical factors that may affect the sensor time period measurement, such as any combination of temperature, pressure, altitude, and density.

Compensated sensor time period 210 of sensor assembly 10 may be compensated for temperature. For example, the at least one temperature sensor 112 may indicate that sensor assembly 10 is a different temperature than the reference calibration temperature. In embodiments, the reference calibration temperature may be 20° C. Temperature may affect the stiffness of sensor assembly 10, introducing an offset into the sensor time period measured. In an embodiment, compensated sensor time period 210 may be determined by calculating an offset for average sensor time period 209 based on average temperature 208.

In an embodiment, the density of ambient air may be measured during an air-point health check. The sensor time period measured may further be affected by atmospheric pressure differences between reference conditions at the factory and a customer site. Atmospheric pressure differences between reference conditions and a customer site may be due to differences in elevation between the test sites. In embodiments, the reference atmospheric pressure may be 101.325 kPa. Pressure fluctuations due to weather changes may also be present, but are less significant than changes in pressure due to elevation. When a health check is performed with a gas that is a different pressure than a reference gas pressure, the difference in pressure may create an offset in the sensor time period measured.

Storage system 204 may further include an altitude 218, a measured density 219, a reference density 220, a density sensitivity 221, a difference density 222, a compensated reference density 223, and a density time period offset 224. Altitude 218 may represent the altitude at which the sensor is installed. In embodiments, altitude 218 may be input by a user and saved to storage system 204. For example, altitude 218 may be input at the beginning of a health check, upon installation of a sensor at a customer site, or at any other time. In other embodiments, altitude 218 may be received via electronic message at meter electronics 20.

Measured density 219 may be measured during a health check using sensor assembly 10 as described above. Reference density 220 may be a density measured by vibrating element meter 5 under reference conditions with ambient atmospheric gas. Reference density 220 may be compensated for changes in density due to altitude, temperature, and pressure to generate compensated reference density 223:

$$\rho_1 = \rho_0 \frac{T_0}{T_1} \frac{P_1}{P_0}$$

In the above equation, $\rho_0$, $T_0$, and $P_0$ represent the respective reference density, temperature, and pressure. Compensated reference density 223 is represented by $\rho_1$. $T_1$ is the temperature of the ambient air at the health check site. For example, $T_1$ may represent a temperature of the plurality of temperatures 206 or average temperature 208. $P_1$ is the pressure of ambient air at the health check site. $P_1$ may be estimated using the following equation:

$$P_1 = P_0(1 - 2.255.77^{-5} \times h)^{5.2558}$$

where h represents the altitude of the test site in units of meters.

In a further embodiment, measured density 219 may be compensated to reference altitude, temperature, and pressure.

Density sensitivity 221 and difference density 222 may be used to calculate a density time period offset 224. Difference density 222 represents the difference between compensated reference density 223 and measured density 219. This is not intended to be limiting, however. In other embodiments, difference density 222 may represent the difference between a reference density and a measured density compensated to reference altitude, pressure, and temperature.

Density sensitivity 221 is a measure of the accuracy of a meter as affected by the material in the meter, and is defined as the following for a fork-type density meter:

Density sensitivity=$K_1$+2×$K_2$×(temperature compensated sensor time period)

Density sensitivity 221 is defined as the following for a gas density meter:

Density sensitivity=2×$K_2$×(temperature compensated sensor time period)

In both of the above density sensitivity equations, $K_1$ and $K_2$ represent calibration constants that may be determined during a meter calibration process. For example, $K_1$ and $K_2$ may be determined by a calibration process using two different fluids having densities known to a high accuracy.

Density time period offset 224 is the offset that may be attributed to a difference in fluid density between a health point check and a density of that fluid at reference conditions. Density time period offset 224 may be determined with the following equation:

$$\text{Density time period offset} = \frac{\text{density difference}}{\text{density sensitivity}}$$

In embodiments, density time period offset 224 may be used to further compensate compensated sensor time period 210. In other embodiments, density time period offset 224 may be used to compensate average sensor time period 209, or any of the plurality of sensor time periods 207.

Storage system 204 may further store a reference sensor time period 211 and a sensor time error limit 212. In embodiments, reference sensor time period 211 may be measured at the factory under reference conditions before a sensor assembly is shipped to a client. In other embodiments, reference sensor time period 211 may represent a reference value determined when the meter is installed or configured at a customer site. Reference sensor time period 211 may be specific to a reference pressure, temperature, altitude, and/or fluid density. In an embodiment, reference sensor time period 211 may be determined with vibrating elements of a sensor filled with ambient gas at sea level. In other embodiments, reference sensor time period 211 may be determined with the vibrating elements of a sensor under a vacuum. In further embodiments, reference sensor time period 211 may be determined under any combination of temperature and pressure, and may include any reference fluid. For example, water may be used as a reference fluid.

Sensor time error limit 212 represents the maximum permissible difference between reference sensor time period 211 and a compensated sensor time period 210 allowable to provide a finding of validity for a meter sensor.

Storage system 204 may further include a sensor valid indicator 225. Sensor valid indicator 225 may be set upon a determination of whether the difference between compensated sensor time period 210 and reference sensor time period 211 is less than a sensor time error limit 212. Sensor valid indicator 225 may indicate whether sensor assembly 10 may provide accurate measurements of mass flow, density, viscosity, or any other measurement. In embodiments, meter electronics 20 may indicate the status of sensor valid indicator 225 by toggling a light or a display on vibrating element meter 5. In other embodiments, meter electronics 20 may indicate that sensor assembly 10 is valid by sending an electronic report to another computing device.

In determining the validity of a sensor assembly with existing health check methodologies, sensor stability may present a further limitation to receiving accurate results. A meter that is not in a stable or a steady state may provide sensor time period measurements that wander over a wide range of values, providing false results. Storage system 204 further includes a standard deviation temperature 213, a standard deviation sensor time period 214, a standard deviation sensor time period limit 215, a standard deviation temperature limit 216, and a condition stable indicator 217 to address this possible limitation. Standard deviation temperature 213 represents the standard deviation of plurality of temperatures 206. Standard deviation sensor time period 214 represents the standard deviation of plurality of sensor time periods 207.

Standard deviation temperature limit 216 may represent the maximum standard deviation temperature 213 that a stable sensor may indicate. Standard deviation temperature 213 may be elevated when the temperature of a sensor assembly 10 is changing rapidly. When the standard deviation temperature 213 is greater than standard deviation temperature limit 216, the vibrating meter may not be able to provide reliable measurements, and a health check may not produce accurate results.

Standard deviation sensor time period 214 may be elevated for any number of reasons, including when environmental or testing conditions change rapidly. Standard deviation sensor time period limit 215 may represent the maximum sensor time period standard deviation that a stable sensor may indicate. When the standard deviation sensor time period 214 is greater than standard deviation sensor time period limit 215, then the vibrating meter may not be able to provide reliable measurements, and a health check may not produce accurate results.

A condition stable indicator 217 may be set to indicate whether the sensor is determined to be stable. In embodiments, condition stable indicator 217 may be indicated on a light or another display for a user. In other embodiments, condition stable indicator 217 may be sent via electronic report to another computing device.

In an embodiment, the storage system 204 includes routines that are executed by the processing system 203. For example, the storage system 204 stores a sensor verification routine 205. Meter electronics 20 may initiate and operate sensor verification routine 205 in order to validate a sensor assembly 10. In embodiments, sensor verification routine 205 may perform a health check to determine the validity of a sensor assembly, and indicate the results via sensor valid indicator 225 using the methods discussed above. In other embodiments, sensor verification routine 205 may determine whether the sensor assembly 10 provides stable measurements and indicate the results via condition stable indicator 217, as described above.

Figure 3:
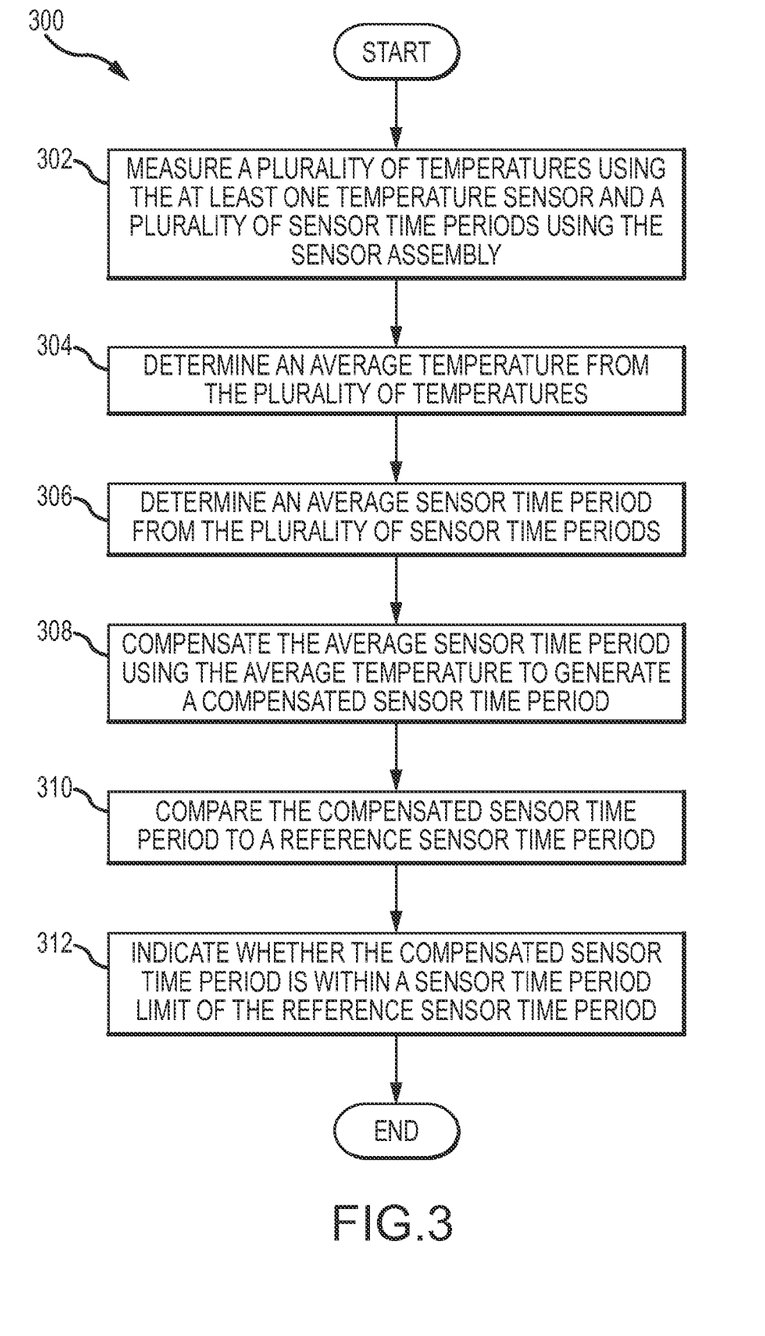
FIG. 3 depicts method 300 according to an embodiment of the Application.
Figure 4:
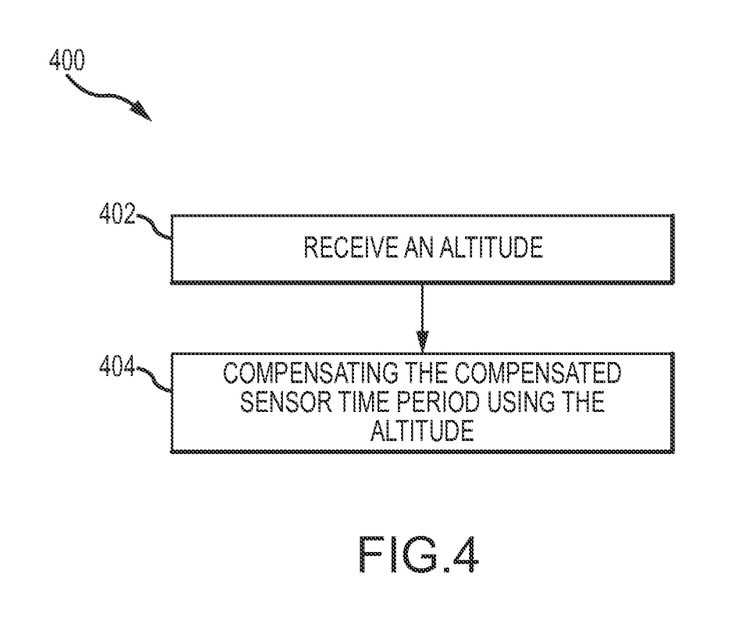
FIG. 4 depicts method 400 according to an embodiment of the Application.
Figure 5:
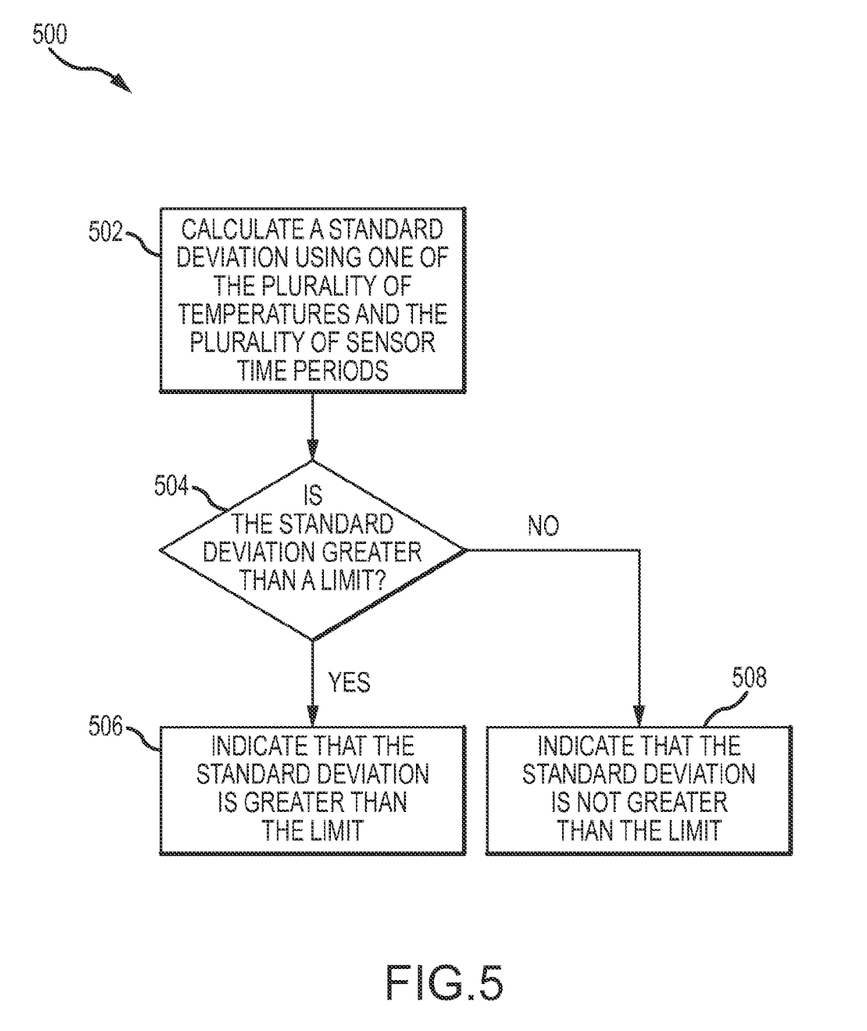
FIG. 5 depicts method 500 according to an embodiment of the Application.

FIGS. 3-5 depict sensor verification methods 300, 400, and 500 respectively. Sensor verification methods 300, 400, and 500 represent example embodiments of sensor verification routine 205. Processing system 203 may be configured to perform the necessary signal and data processing to execute sensor verification routine 205, which may include performing any combination of sensor verification methods 300, 400, and 500.

Sensor verification method 300 of FIG. 3 begins with step 302. In step 302, a plurality of temperatures are measured using the at least one temperature sensor and a plurality of sensor time periods are measured using the sensor assembly 10. For example, plurality of temperatures 206 may be measured using temperature sensor 112. In embodiments, plurality of temperatures 206 may be measured using more than one temperature sensor coupled to any part of sensor assembly 10. Plurality of sensor time periods 207 may be determined by vibrating driver 16 and receiving a vibratory response with pickoff/detection sensor 17 at meter electronics 20.

In embodiments, step 302 may further include cleaning the sensor assembly 10. For example, the insides or outsides of housing 11, vibrating member 12, inlet end 13, fluid apertures 15, driver 16, pickoff/detection sensor 17, or cylinder 50 may be cleaned with solvent or any other method commonly known to those skilled in the art.

In embodiments, step 302 may further include filling the sensor assembly 10 with ambient air.

In embodiments, step 302 may further include placing the sensor assembly 10 under a vacuum.

In embodiments, step 302 may further include filling the sensor assembly 10 with a fluid having an accurately known density. For example, the sensor assembly may be filled with water.

Method 300 continues with step 304. In step 304, an average temperature is determined from the plurality of temperatures. For example, average temperature 208 may be determined by averaging plurality of temperatures 206, as described above.

Method 300 continues with step 306. In step 306, an average sensor time period is determined from the plurality of sensor time periods. For example, average sensor time period 209 may be determined by averaging plurality of sensor time periods 207, as described above.

Method 300 continues with step 308. In step 308, the average sensor time period is compensated using the average temperature to generate a compensated sensor time period. For example, average sensor time period 209 may be compensated using average temperature 208 to generate compensated sensor time period 210, as described above.

Method 300 continues with step 310. In step 310, the compensated sensor time period is compared to a reference sensor time period. For example, the compensated sensor time period 210 may be compared to reference sensor time period 211, as described above.

Method 300 continues with step 312. In step 312, it is indicated whether the compensated sensor time period is within a sensor time period error limit of the reference sensor time period. For example, it may be indicated whether compensated sensor time period 210 is within sensor time error limit 212 of reference sensor time period 211, as described above.

In embodiments, sensor validation method 400 may be performed in addition to method 300. Method 400 of FIG. 4 begins with step 402. In step 402, an altitude is received. The altitude is the height of the location of the sensor above sea level. For example, altitude 218 may be received, as described above.

Method 400 continues with step 404. In step 404, the compensated sensor time period is compensated using the altitude. For example, compensated sensor time period 210 may be compensated using altitude 218, as described above.

In embodiments, step 404 may further include measuring a density of a fluid using the sensor assembly, and compensating the compensated sensor time period for a difference in density between the reference density and the measured density using the altitude. For example, measured density 219 may be measured using the sensor assembly 10. Altitude 218 may be used to compensate any of the plurality of sensor time periods 207, the average sensor time period 209, or the compensated sensor time period 210, as described above.

In embodiments, sensor validation method 500 may be performed in addition to methods 300 and/or 400. As FIG. 5 depicts, method 500 begins with step 502. In step 502, a standard deviation is calculated using one of the plurality of temperatures and the plurality of sensor time periods. For example, standard deviation temperature 213 may be calculated using plurality of temperatures 206, or standard deviation sensor time period 214 may be calculated using plurality of sensor time periods 207, as described above.

Method 500 continues with step 504. In step 504, it is determined whether the standard deviation is greater than a limit. For example, it may be determined whether standard deviation temperature 213 is greater than standard deviation temperature limit 216, or it may be determined whether standard deviation sensor time period 214 is greater than standard deviation sensor time period limit 215, as described above. In embodiments, method 500 may be performed twice, evaluating each of standard deviation temperature 213 and standard deviation sensor time period 214.

If in step 504 it is determined that the standard deviation is greater than a limit, method 500 continues with step 506. If in step 504 it is determined that the standard deviation is not greater than a limit, method 500 continues with step 508. In step 506 it is indicated that a condition is unstable. In step 508 it is indicated that a condition is stable. For example, condition stable indicator 217 may be used to indicate whether the condition of sensor assembly 10 is stable. In an embodiment, meter electronics 20 may indicate whether a condition is stable by toggling an indicator light or otherwise providing a display for a user. In another embodiment, meter electronics 20 may indicate whether a condition is stable by sending an electronic report. Other methods of indicating the stability of sensor assembly 10 are also contemplated by this Application, as will be understood by those who are skilled in the art.

The detailed descriptions of the above embodiments are not exhaustive descriptions of all embodiments contemplated by the inventors to be within the scope of the Application. Indeed, persons skilled in the art will recognize that certain elements of the above-described embodiments may variously be combined or eliminated to create further embodiments, and such further embodiments fall within the scope and teachings of the Application. It will also be apparent to those of ordinary skill in the art that the above-described embodiments may be combined in whole or in part to create additional embodiments within the scope and teachings of the invention.

Thus, although specific embodiments of, and examples for, the Application are described herein for illustrative purposes, various equivalent modifications are possible within the scope of the Application, as those skilled in the relevant art will recognize. The teachings provided herein may be applied to other meters, and not just to the embodiments described above and shown in the accompanying figures. Accordingly, the scope of the Application should be determined from the following claims.

What is claimed is:

1. A vibrating element meter (5) for meter health verification, the vibrating element meter (5) comprising:
a sensor assembly (10) including a vibrating member (12), a pickoff/detection sensor (17), and a driver (16) configured to vibrate the vibrating member (12);
at least one temperature sensor (112) coupled to the sensor assembly; and
meter electronics (20) coupled to the pickoff/detection sensor (17), the driver (16), and the at least one temperature sensor (112), with the meter electronics (20) being configured to measure a plurality of temperatures using the at least one temperature sensor (112) and to measure a sequence of driver generated sensor signal periods detected by the pickoff/detection sensor (17), wherein the meter electronics determine an average temperature from the plurality of temperatures, determine an average sensor signal period using the average temperature to generate a compensated sensor signal period, compare the compensated sensor signal period to a reference sensor signal period, and indicate whether the compensated sensor signal period is within a sensor signal period error limit of the reference sensor signal period.

2. The vibrating element meter (5) of claim 1, wherein measuring the plurality of temperatures (206) using the temperature sensor (112) and the sequence of sensor signal periods (207) using the sensor assembly (10) further comprises filling the sensor assembly (10) with ambient air.

3. The vibrating element meter (5) of claim 1, wherein measuring the plurality of temperatures (206) using the temperature sensor (112) and the sequence of sensor signal periods (207) using the sensor assembly (10) further comprises placing the sensor assembly (10) under a vacuum.

4. The vibrating element meter (5) of claim 1, wherein measuring the plurality of temperatures (206) using the temperature sensor (112) and the sequence of sensor signal periods (207) using the sensor assembly (10) further comprises filling the sensor assembly (10) with or inserting the sensor assembly into a fluid having an accurately known density.

5. The vibrating element meter (5) of claim 1, wherein the meter electronics (20) is further configured to calculate a standard deviation using one of the plurality of temperatures (206) and the sequence of sensor signal periods (207), compare the standard deviation to a limit, and indicate whether the standard deviation is greater than the limit.

6. The vibrating element meter (5) of claim 1, wherein the meter electronics (20) is further configured to receive an altitude (218), and compensate the compensated sensor time period (210) using the altitude (218).

7. The vibrating element meter (5) of claim 6, wherein the meter electronics (20) is further configured to measure a density of a fluid using the sensor assembly (10), and compensate the compensated sensor time period (210) for a difference in density between the reference density (220) and the measured density (219) using the altitude (218) and the average temperature (208).

8. A method for health verification of a sensor, the method comprising the steps of:
measuring a plurality of temperatures (206) of a fluid flow using at least one temperature sensor (112) coupled to a sensor assembly and to measure a sequence of driver generated sensor signal periods (207) detected by a pickoff/detection sensor (17) of the sensor assembly (10), the sensor assembly (10) further including a vibrating member (12), and a driver (16) configured to vibrate the vibrating member (12);
determining an average temperature (208) from the plurality of temperatures (206);
determining an average sensor signal period (209) using the average temperature (208) to generate a compensated sensor signal period (210);
comparing the compensated sensor signal period (210) to a reference sensor signal period (211); and
indicating whether the compensated sensor time period (210) is within a sensor time error limit (212) of the reference sensor signal period (211).

9. The method of claim 8, further comprising:
cleaning the sensor assembly (10).

10. The method of claim 8, wherein measuring the plurality of temperatures (206) and the sequence of sensor signal periods (207) using the sensor assembly (10) further comprises filling the sensor assembly (10) with ambient air.

11. The method of claim 8, wherein measuring the plurality of temperatures (206) and the sequence of sensor signal periods (207) using the sensor assembly (10) further comprises placing the sensor assembly (10) under a vacuum.

12. The method of claim 8, wherein measuring the plurality of temperatures (206) and the sequence of sensor signal periods (207) using the sensor assembly (10) further comprises filling the sensor assembly (10) with or inserting the sensor assembly (10) into a fluid having an accurately known density.

13. The method of claim 8, further comprising the steps of:
calculating a standard deviation using one of the plurality of temperatures (206) and the sequence of sensor signal periods (207);
comparing the standard deviation to a limit; and
indicating whether the standard deviation is greater than the limit.

14. The method of claim 8, further comprising the steps of:
receiving an altitude (218); and
compensating the compensated sensor time period (210) using the altitude (218).

15. The method of claim 14, wherein compensating the compensated sensor time period (210) using the altitude (218) further includes:
measuring a density of a fluid using the sensor assembly (10); and
compensating the compensated sensor time period (210) for a difference in density between the reference density (220) and the measured density (219) using the altitude (218) and the average temperature (208).

16. A method for health verification of a sensor, the method comprising the steps of: measuring a plurality of temperatures (206) using at least one temperature sensor (112) coupled to a sensor assembly and a sequence of driver generated sensor signal periods (207) detected by a pickoff/detection sensor (17) of the sensor assembly (10), the sensor assembly (10) further-including a vibrating member (12), and a driver (16) configured to vibrate the vibrating member (12); calculating a first standard deviation using both a first data set comprising a plurality of temperatures (206) and a second standard deviation using a sequence of sensor signal periods (207); comparing the first and second standard deviation (213, 214) to a respective first and second limit (215,216); and indicating whether the respective first and second standard deviation (213, 214) is greater than the respective first and second limit (215,216).

17. The method of claim 16, further comprising the steps of:
calculating a second standard deviation (213, 214) using a second data set comprising one of the plurality of temperatures (206) or the sequence of sensor signal periods (207), wherein the first data set is different from the second data set;
comparing the second standard deviation (213, 214) to a second limit (215,216); and
indicating whether the second standard deviation (213, 214) is greater than the second limit (215,216).

* * * * *

UNITED STATES PATENT AND TRADEMARK OFFICE
CERTIFICATE OF CORRECTION

PATENT NO. : 10,215,677 B2  
APPLICATION NO. : 14/778958  
DATED : February 26, 2019  
INVENTOR(S) : Simon P. H. Wheeler Page 1 of 1

It is certified that error appears in the above-identified patent and that said Letters Patent is hereby corrected as shown below:

In the Specification

Column 8, Line 19 that portion of the formula reading:
"$P_1 = P_0 (1 - 2.255.77^{-5} \times h)^{5.2558}$"

Should read:
-- $P_1 = P_0 (1 - 2.25577^{-5} \times h)^{5.2558}$ --

Signed and Sealed this  
Twenty-fourth Day of December, 2019

Andrei Iancu  
*Director of the United States Patent and Trademark Office*